(12) United States Patent
Ip et al.

(10) Patent No.: US 8,172,908 B2
(45) Date of Patent: May 8, 2012

(54) IMPLANT FOR TISSUE ENGINEERING

(75) Inventors: Wing Yuk Ip, Hong Kong (CN); Chi Keung Yuen, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 440 days.

(21) Appl. No.: 12/342,812

(22) Filed: Dec. 23, 2008

(65) Prior Publication Data

US 2009/0187258 A1     Jul. 23, 2009

Related U.S. Application Data

(60) Provisional application No. 61/021,709, filed on Jan. 17, 2008.

(51) Int. Cl.
 A61F 2/02      (2006.01)
(52) U.S. Cl. .................... 623/23.72; 623/23.75
(58) Field of Classification Search .............. 606/151; 623/23.72, 23.75, 23.76; 600/37; 424/422–424, 424/682; 514/21.92
 See application file for complete search history.

(56) References Cited

U.S. PATENT DOCUMENTS

| | | | |
|---|---|---|---|
| 3,687,135 A | 8/1972 | Stroganov et al. | |
| 6,428,546 B1 * | 8/2002 | Cancel et al. | 606/151 |
| 6,719,987 B2 * | 4/2004 | Langford et al. | 424/422 |
| 7,166,570 B2 * | 1/2007 | Hunter et al. | 514/21.92 |
| 7,824,701 B2 * | 11/2010 | Binette et al. | 424/423 |
| 7,879,367 B2 * | 2/2011 | Heublein et al. | 424/682 |
| 2005/0079088 A1 | 4/2005 | Wirth et al. | |

FOREIGN PATENT DOCUMENTS

DE    1 953 241    5/1971

OTHER PUBLICATIONS

ASTM International: Designation: B 94-07, "Standard Specification for Magnesium-Alloy Die Castings," Dec. 2007, pp. 1-6.
McBride, E. D., "Absorbable Metal in Bone Surgery: A Further Report on the Use of Magnesium Alloys," *Journal of American Medical Association*, Dec. 31, 1938, vol. 111, No. 27, pp. 2464-2467.
Mendes, D. G. et al., "Maturation of Composite Ligament," *Clinical Orthopaedics and Related Research*, Sep. 1988, vol. 234, pp. 291-295.
Staiger, M. P. et al., "Magnesium and its alloys as orthopedic biomaterials: A review," *Biomaterials*, 2006, vol. 27, pp. 1728-1734.
Witte, F. et al., "Biodegradable magnesium scaffolds: Part I: Appropriate inflammatory response," *Journal of Biomedical Materials Research Part A*, 2007, vol. 81A, pp. 748-756.
Yuen, C. K. et al., "Resorbable metallic implant: findings from an animal model," *Advanced Materials Research*, 2008, vols. 47-50, pp. 604-607.

* cited by examiner

*Primary Examiner* — Julian Woo
(74) *Attorney, Agent, or Firm* — Saliwanchik, Lloyd & Eisenschenk

(57) ABSTRACT

The present invention relates to uses of resorbable medical implants that are metallic or semi-metallic, to produce soft tissues, membranous tissues, organs or organ parts within the body by fibrosis. The present invention further relates to such uses when the implants are made of specified alloys or metals, e.g. magnesium and its alloys. The present invention further relates to such uses when the implant is surface modified. The present invention further relates to such uses when the implant is pre-implanted at another part of the body before implantation into the target site.

21 Claims, 3 Drawing Sheets

| Rod/wire | Bent wire | Spring | Interweaving into a thread, string, etc (for one or more than one compositions) | 2D or 3D mesh (for one or more than one compositions) | Application of more than one piece of the specified biomaterial (for one or more than one compositions) |

IMPLANT FOR TISSUE ENGINEERING

CROSS-REFERENCE TO A RELATED APPLICATION

The subject application claims the benefit of U.S. Provisional Application Ser. No. 61/021,709, filed Jan. 17, 2008, which is incorporated herein by reference in its entirety.

FIELD OF THE INVENTION

This invention relates generally to the use of resorbable metallic medical implants in the generation and/or regeneration of soft tissues, membranous tissues, or organs. The implant may be surface modified and/or pre-implanted into another part of the body before implantation into the target site.

BACKGROUND OF THE INVENTION

Resorbable (alternatively called absorbable, degradable, bioabsorbable, bio-absorbable, bioresorbable, bio-resorbable, biodegradable, bio-degradable, biocorrodible or bio-corrodible) implants have to date been generally prepared from polymers. Unfortunately, the use of polymers in implants has two serious disadvantages. First, plasticizers harmful to the body can be released from the implant. Furthermore, the mechanical properties of the polymers are often unsatisfactory.

Since the beginning of the 20th century it has been known that implants made of magnesium and its alloys are easily absorbable and biocompatible. The absorbability in the body is based on the corrosion of magnesium in saline immersions. Its essential character for the body's functions and the elimination of excess doses via the urinary tract qualify magnesium as a basic implant substance with a high level of physical and chemical biocompatibility.

The average distribution of magnesium in the body mass is 470 mg/kg, the recommended daily dose is 200 to 300 mg/d MgSO4. Magnesium also has an antiarrhythmic effect and lowers blood pressure and sensitivity to pain. The maximum dose for short-term infusion in a human weighing 75 kg is 57.6 mg pure magnesium. Blood plasma contains, for example, 107 mMol/l, and gastric juice contains 160 mval/l of magnesium chloride ions.

The developments in the first Mg period before World War Two (Verbrugge 1933, McBride 1938, Lambotte 1932) did not result in alloys that corrode sufficiently slowly. The developments in the second Mg period during the Cold War (Stroganov, DE-OS 1 953 241) provided alloys with greater corrosion resistance whose cadmium additive was intended to accelerate bone fusion, but whose toxicity substantially limited its use.

Other more recent magnesium alloys contain rare earth metals, preferably in addition to lithium. With these alloys, the absorption of the implant is considerably delayed, but with these materials there is still an appreciable development of hydrogen and gas pockets in the tissue. For many applications, the rate of corrosion of the alloys containing rare earth metals is still too high, since the stability losses associated with absorption occur too early in the healing or tissue formation process.

The use of surface modifications on such resorbable metallic implants has been mentioned in US20050079088, which aims to use surface modification to improve mechanical and corrosion properties.

It is difficult to culture cells onto resorbable metallic material in a physiologically relevant environment because the ions released and/or the change in pH is likely to harm cells. For example, it is known that the alkaline environment produced by corroding magnesium can kill cells.

However, even if the modification were considered successful, the application would still be limited to hard tissues. Application to soft tissues, membranous tissues, organs or organ parts would appear to be unsuitable because of the perceived rigidity of magnesium or other metallic materials, regardless of the resorbability.

Therefore, the use of resorbable metallic materials for the application on soft tissues, membranous tissues or organs especially for the generation or regeneration of such tissues is a largely unexplored field. Such generation or regeneration of tissues with engineering technique may also be called "tissue engineering".

From experiments of our team, a tough, dense layer of soft tissue is formed on a piece of magnesium implanted subcutaneously into a mouse. According to literature (Witte F, Ulrich H et. al. (2007) J Biomed Mater Res 81A: 748-756), this layer should be cell-infiltrated collagen, produced by "foreign body response" in the form of fibrosis on biomaterials.

The principle of fibrosis induction had actually been used in the 1980s (Mendes D G, Soudry M, et. al. (1988) Clinical Orthopaedics and Related Research 234:291-295) for the regeneration of ligaments, although without much popularity, and the bio-material used was carbon fiber. Carbon fiber is too stiff, and it does not have the required bioactivity. Either of these factors is sufficient to create the unpopularity of such prior art.

Also intravascular fibrosis-inducing agents are used by some investigators to generate biological tissues by fibrosis for the purpose to facilitate cell anchoring.

BRIEF SUMMARY OF THE INVENTION

The subject invention provides an innovative use of metallic and semi-metallic implants for the generation and/or regeneration of soft tissues and/or membranous tissues and/or organs. In accordance with the subject invention, the effect of self-induced collagen formation (on a piece of metallic or semi-metallic implant that can be absorbed by the body) by fibrosis is used to induce the natural self-production of such tissue in the body.

The tissues to which the materials and methods of the subject invention can be applied include, but are not limited to, ligament, tendon, periodontal fiber, skin, internal organs, muscles and vessels, but excluding bone and cartilage.

In one aspect, the present invention pertains to the use of metallic or semi-metallic materials in resorbable medical implants, for an application of soft tissues such as ligaments, tendons and periodontal fibers.

In another aspect, the present invention pertains to the use of metallic or semi-metallic materials in resorbable medical implants, for the generation and/or regeneration of organs and membranous tissues, but excluding bone.

In a specific embodiment, the present invention pertains to the use of metallic or semi-metallic materials in resorbable metallic implants, for the generation and/or regeneration of soft tissue for hernia correction.

One or more of the following features may be used to further characterize the subject invention: the implant is, or comprises, magnesium; the implant is, or comprises a magnesium alloy; the implant is, or comprises tungsten; the implant is, or comprises a tungsten alloy; the implant is, or comprises zinc; the implant is, or comprises a zinc alloy; the implant is, or comprises aluminum; the implant is, or comprises an aluminum alloy; the implant is, or comprises iron; the implant is, or comprises an iron alloy; the implant is, or comprises steel; the implant is, or comprises manganese; the implant is, or comprises a manganese alloy; the implant is, or comprises calcium; the implant is, or comprises a calcium alloy; the implant is, or comprises zirconium; the implant is, or comprises a zirconium alloy; the implant is, or comprises silicon; the implant is, or comprises a silicon alloy.

In a further aspect, the implant may comprise a non-metallic solid. The non-metallic solid may be in one or more of the following forms: powder, fiber, film, crystal, nanocrystal, nanoparticle, nano-film or nano-fiber. More than one chemical composition of non-metallic solid can be present. The non-metallic solid can be one or more of the following elements or compounds: carbon, carbonate compound, phosphate compound, non-metallic compound of metallic element, non-metallic compound of semi-metallic element, polymer, anticoagulant, or their combinations.

The implant can be surface modified in accordance with one or more of the following processes: oxidation, nitriding, solution immersion, anodization, deposition, electrolytic deposition, precipitation, immersion into molten metal, immersion into molten alloy, immersion into molten semi-metal, immersion into collagen, immersion into organic material, plasma immersion, plasma deposition, plasma spraying, flame spraying, chemical vapour deposition, physical vapour deposition, powder deposition, powder immersion, plasma immersion, plasma immersion ion implantation, electric arc deposition, painting, coating, heat treatment, cold treatment, thermomechanical processing, polishing, diffusion alloying, melt alloying, incubation in cell culture condition rapid prototyping, selective laser sintering, solution spraying, particulate leaching, etching, evaporation, sublimation, or sterilization; and the surface modification may cover the whole surface or only a portion of it.

In a further aspect, the solution immersion is further characterized in that it comprises one or more of the following: alkali treatment, hot alkali treatment, phosphate buffered saline immersion, cell culture medium immersion, body fluid immersion, simulated body fluid immersion, serum immersion, phosphate solution immersion, acid treatment, immersion into collagen solution, immersion into organic material solution, immersion into growth factor solution, immersion into solution containing antibiotics, immersion into synthetic growth factor solution, immersion into solution containing synthetic antibiotics, immersion into extracellular matrix solution, immersion into simulated extracellular matrix solution, immersion into growth factor solution with mammal cells, immersion into solution containing antibiotics and mammal cells, immersion into synthetic growth factor solution with mammal cells, immersion into solution containing synthetic antibiotics and cells, immersion into extracellular matrix solution with cells, immersion into simulated extracellular matrix solution with cells.

In a further aspect of the current invention, the implant may be implanted into a part of the body other than the ultimate target site before being retrieved and put at the target site of generation/regeneration.

DETAILED DESCRIPTION OF THE INVENTION

Figure 1A:
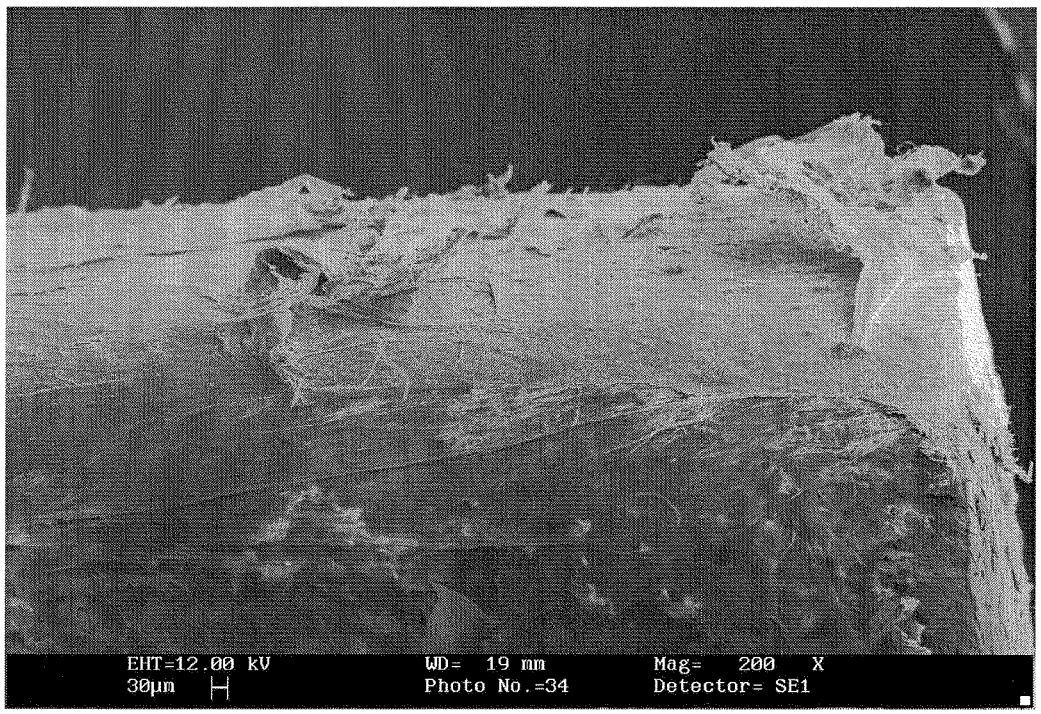
FIG. 1A-B: Well-structured, tough, dense layer of soft tissue formed by fibrosis after subcutaneous implantation of an AM60B rod into a mouse for 1 month (electron microscope photo).
Figure 1B:
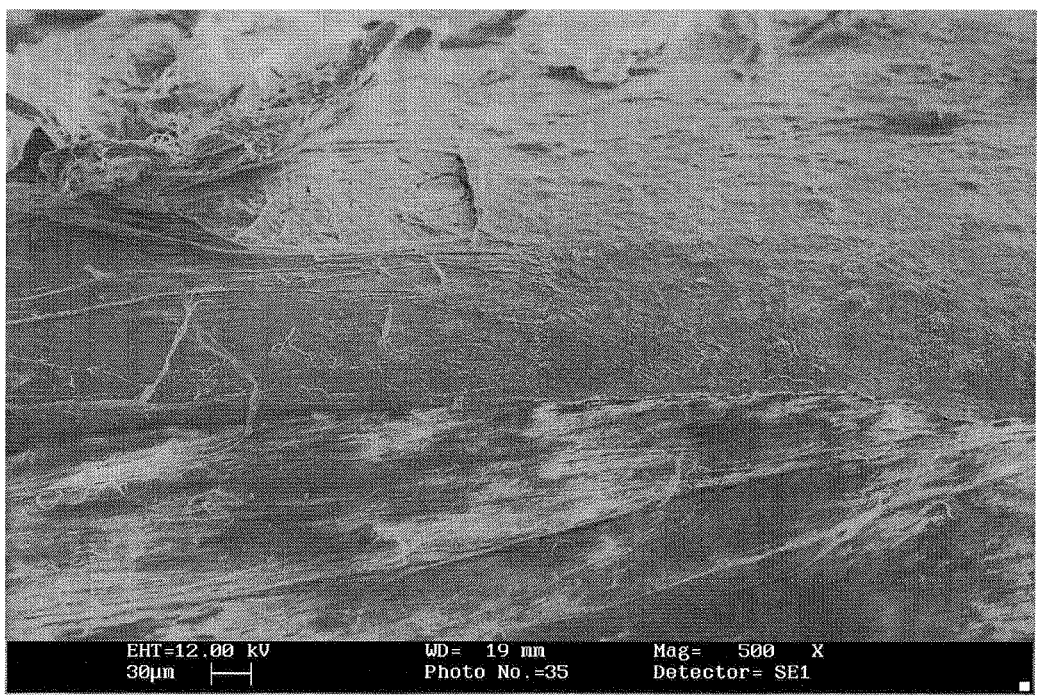
Figure 2:
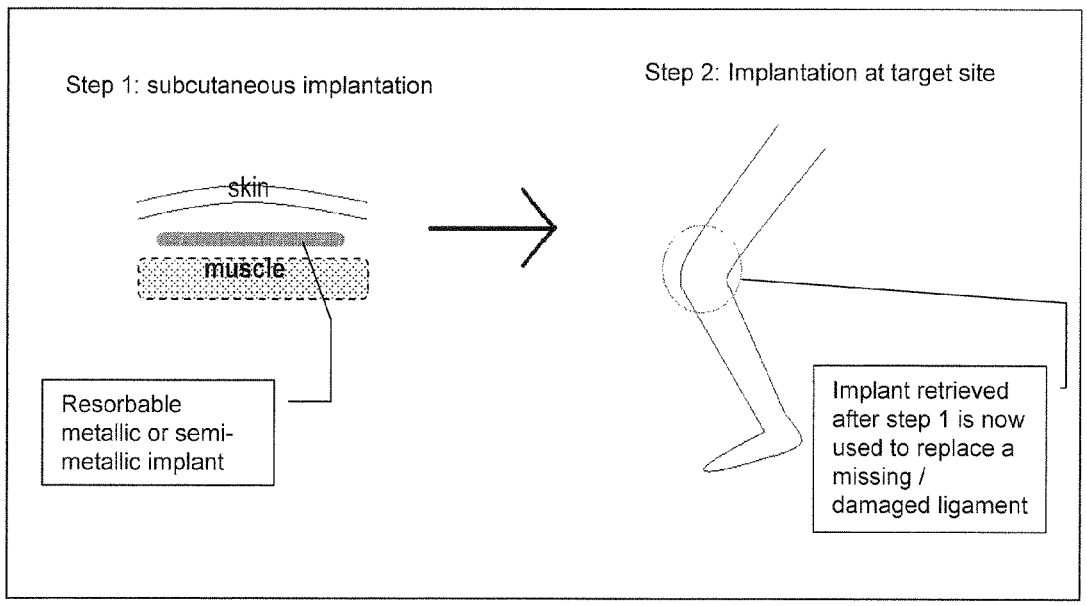
FIG. 2: Subcutaneous pre-implantation before moving the implant to the target site of generation or regeneration.
Figure 3:
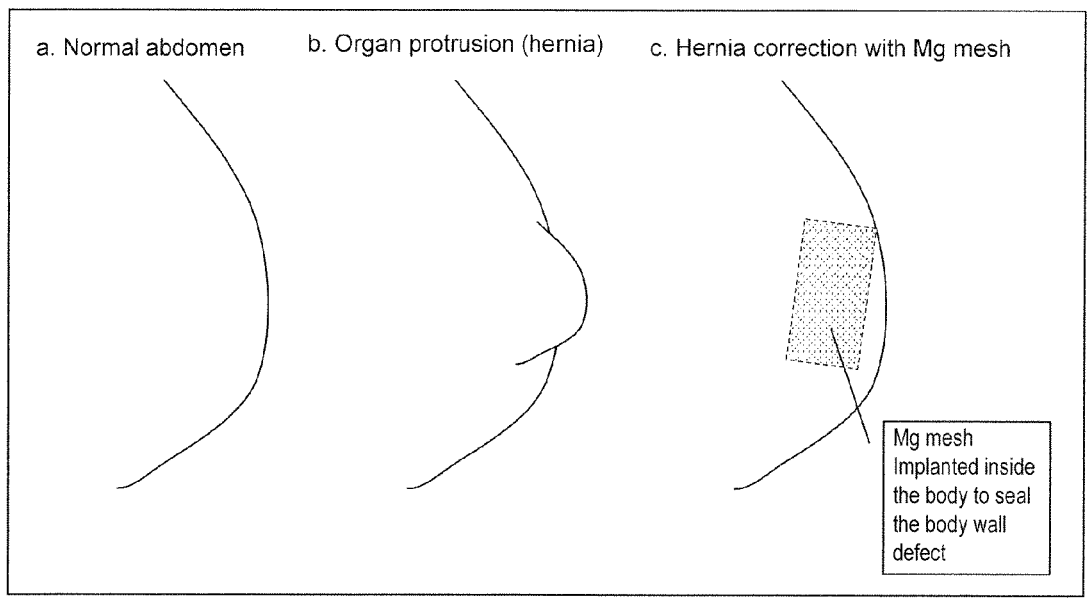
FIG. 3: Example of application for hernia correction.
Figure 4:
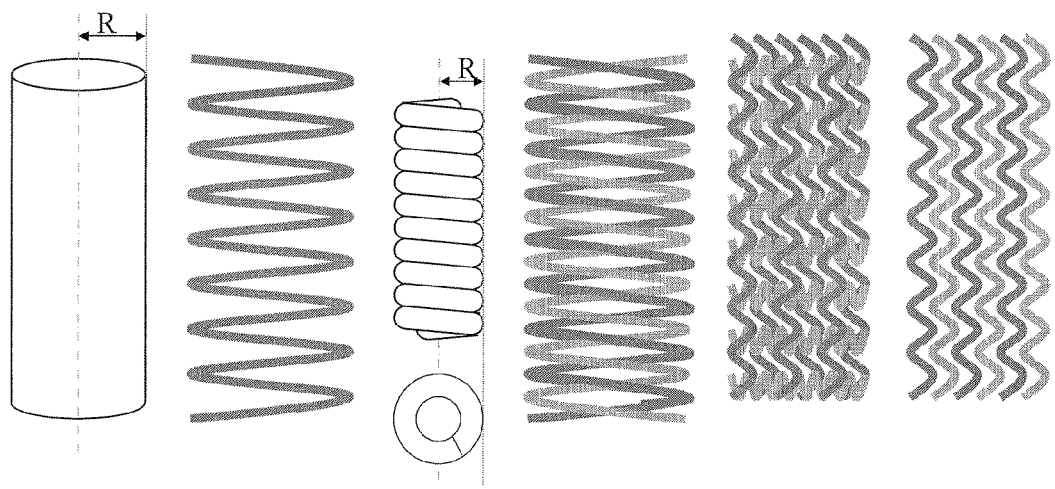
FIG. 4: Examples of specific shapes of implants according to the current invention.

In accordance with the subject invention, tissues produced by the process of fibrosis can be utilized to generate and/or regenerate soft tissues, membranous tissue, or organs within the body. Advantageously, the subject invention provides materials and methods for generating or regenerating such tissues with a biomaterial that has very high bioactivity and low toxicity, combined with good mechanical strength and favorable degradability profile.

The materials and methods of the subject invention can be used for tissue regeneration for various tissues including, but not limited to, ligaments and tendons, which are currently relying on costly and unreliable cell-based therapy, or the transplantation of such tissues removed from another part of the body.

The current invention exploits the phenomenon of fibrosis to generate or regenerate soft tissues, membranous tissues, organs or organ parts within the body. However, two applications, namely the generation and regeneration of cartilage and bones, are intentionally dedicated to the public.

"Fibrosis", "scarring", or "fibrotic response" refers to the formation of fibrous tissue or any excess production, accumulation or deposition of extracellular matrix components (including collagen and other biomolecules) with or without cell infiltration, in response to injury or medical intervention which includes biomaterial implantation, and is referred to as "fibrosis" hereafter. Therapeutic agents that promote fibrosis, which may be called "fibrosis-inducing agents," "scarring agents," "adhesion-inducing agent," "fibrosing agent", and the like, promote fibrosis through one or more mechanisms including: inducing or promoting angiogenesis, stimulating migration or proliferation of soft tissue or connective tissue cells (such as fibroblasts, smooth muscle cells, and vascular smooth muscle cells), inducing ECM production, and/or promoting tissue remodeling.

Other terms, as used herein, are defined as follows:

"Foreign body response" is defined as a reaction of biological tissue to any foreign material in the tissue. "Fibrosis" is one kind of foreign body response. "Foreign body response" in the form of fibrosis is traditionally considered an undesirable "side effect" because it is triggered by an inflammatory response. As a result, past researchers have failed to appreciate any positive aspects of cell-infiltrated collagen formation by fibrosis.

"Soft tissue" refers to tissues that connect, support, or surround other structures and organs of the body. Soft tissue includes muscles, tendons (bands of fiber that connect muscles to bones), fibrous tissues, fat, blood vessels, nerves, stroma, ligaments and synovial tissues other than ligament. Specifically, as used herein, it does not include cartilage or skin.

"Implant" as a noun is used herein at a broad sense, to include any material placed inside the body by any method other than ingestion or inhalation, or placed on the surface of an open wound. "Implant" as a verb refers herein to the process of putting the material inside the body by any method other than ingestion or inhalation.

"Membranous tissue" is used herein to mean any tissue of an animal that forms a sheet or sheath; membranous tissue commonly encloses or delimits a tissue, or divides an organ into separate compartments.

"Cardiovascular tissue" refers to any tissue of the cardiovascular system, and is exemplified to include blood vessels, capillaries, heart, myocardium, heart valves, blood vessel valves, and any membranous or non-membranous tissue of the cardiovascular system.

"Growth factor" refers to a substance that is effective to promote the growth of cells and which, unless added to the culture medium as a supplement, is not otherwise a component of the basal medium. Put another way, a growth factor is a molecule that is not secreted by cells being cultured (including any feeder cells, if present) or, if secreted by cells in the culture medium, is not secreted in an amount sufficient to achieve the result obtained by adding the growth factor exogenously. Growth factors include, but are not limited to, basic fibroblast growth factor (bFGF), acidic fibroblast growth factor (aFGF), epidermal growth factor (EGF), insulin-like growth factor-I (IGF-T), insulin-like growth factor-II (IGF-II), platelet-derived growth factor-AB (PDGF), vascular endothelial cell growth factor (VEGF), activin-A, bone morphogenic proteins (BMPs), insulin, cytokines, chemokines, morphogens, neutralizing antibodies, other proteins, and small molecules.

"Tissue" or "Organ" is used herein to refer to any natural or engineered biological tissue or organ, including, but not limited to, vascularized tissues and avascular tissues, including musculoskeletal tissue, such as cartilage, menisci, muscles, ligaments and tendons, skin, cardiovascular tissue, neuronal tissue, periodontal tissue, glandular tissue, organ tissue, islets of Langerhans, cornea, ureter, urethra, breast tissue, and organs, such as pancreas, bladder, kidney, breast, liver, intestine, heart and sections or pieces thereof.

"Internal organ" herein refers to any organ as defined above, but excluding skin.

The term "resorbable" refers to the ability of materials to be broken down and/or absorbed by normal chemical, biochemical and/or physical processes such as erosion, dissolution, corrosion, degradation, hydrolysis, abrasion, fatigue etc, and their combinations.

The term "collagen" as used herein refers to all forms of collagen, including natural collagen and pro-collagen, or those that have been recombinantly produced, extracted, processed, or otherwise modified. Preferred collagens may be immunogenic or non-immunogenic, soluble or insoluble, and may be in the fibrillar or non-fibrillar form.

In one aspect, the present invention pertains to the use of a metallic or semi-metallic material as a resorbable medical implant, for an application of soft tissues such as ligaments, tendons and periodontal fibers. An application to ligament or tendon regeneration is specifically exemplified herein.

In another aspect, the present invention pertains to the use of a metallic or semi-metallic material as a resorbable medical implant, for generation and/or regeneration of organs and membranous tissues (but excluding cartilage, bone and skin). An application to organ wall and membranous tissues is specifically exemplified herein.

A "hernia" is a protrusion of an organ or part (as the intestine) through connective tissue or through a wall of the cavity (as of the abdomen) in which it is normally enclosed (Merriam-Webster Dictionary). In another aspect, the present invention pertains to the use of a metallic or semi-metallic material as a resorbable metallic implant, for generation and regeneration of soft tissue for hernia correction. An application to abdominal hernia is specifically exemplified herein.

In another aspect, the present invention pertains to the use of a metallic or semi-metallic material as a resorbable medical material applied on the surface, for generation and/or regeneration of skin.

One or more of the following features may further define the invention: the implant is, or comprises, magnesium; the implant is, or comprises a magnesium alloy; the implant is, or comprises tungsten; the implant is, or comprises a tungsten alloy; the implant is, or comprises zinc; the implant is, or comprises a zinc alloy; the implant is, or comprises aluminum; the implant is, or comprises an aluminum alloy; the implant is, or comprises iron; the implant is, or comprises an iron alloy; the implant is, or comprises steel; the implant is, or comprises manganese; the implant is, or comprises a manganese alloy; the implant is, or comprises calcium; the implant is, or comprises a calcium alloy; the implant is, or comprises zirconium; the implant is, or comprises a zirconium alloy; the implant is, or comprises silicon; the implant is, or comprises a silicon alloy.

Preferred embodiments include pure magnesium of purity 99.95% to 99.9999%, or magnesium alloys with aluminum 0-16 wt. %, calcium 0-5 wt. %, rare earth metals 0-8 wt. %, lithium 0-5 wt. %, and manganese 0-5 wt. %. Preferably, the implants of the subject invention are not in particle or powder form.

In certain specific embodiments, the metal, semi-metal or alloy part of the implant is manufactured by die casting, investment casting, solvent casting, injection moulding, compression moulding, blow moulding, extrusion, intrusion, laminating, sintering, forging, stamping, welding, lathing, tooling, machining, or a combination thereof.

The raw material for manufacturing the metal, semi-metal or alloy part of the implant can be a metal. The raw material for manufacturing the metal, semi-metal or alloy part of the implant can also be a non-metallic compound of the metal, semi-metal or alloy.

In certain embodiments, the metal or semi-metal part of the implant contains not more than 40% of non-metallic solid, or not more than 10% of non-metallic solid, or not more than 3% of non-metallic solid.

The non-metallic solid in the metal, semi-metal or alloy part of the implant can be in the form of powder, fiber, crystal, nanocrystal, nanoparticle or nano-fiber, or a combination thereof. More than one chemical composition of non-metallic solid can be present.

The non-metallic solid can be one or more of the following elements or compounds: carbon, carbonate compound, phosphate compound, non-metallic compound of metallic element, non-metallic compound of semi-metallic element, polymer, anticoagulant, or their combinations. For a preferred embodiment, the mass of the non-metallic solid is less than 20% of the total mass of the implant.

The implant can be surface modified utilizing, for example, one or more of the following processes: oxidation, nitriding, solution immersion, anodization, deposition, electrolytic deposition, precipitation, immersion into molten metal, immersion into molten alloy, immersion into molten semi-metal, immersion into collagen, immersion into organic material, plasma immersion, plasma deposition, plasma spraying, flame spraying, chemical vapour deposition, physical vapour deposition, powder deposition, powder immersion, plasma immersion, plasma immersion ion implantation, electric arc deposition, painting, coating, heat treatment, cold treatment, thermomechanical processing, polishing, diffusion alloying, melt alloying, incubation in cell culture condition, rapid prototyping, selective laser sintering, solution spraying, particulate leaching, etching, evaporation, sublimation, or sterilization.

In a further aspect, the solution immersion is further characterized in that it comprises one or more of the following: alkali treatment, hot alkali treatment, phosphate buffered saline immersion, cell culture medium immersion, body fluid immersion, simulated body fluid immersion, serum immersion, phosphate solution immersion, acid treatment, immersion into collagen solution, immersion into organic material solution, immersion into growth factor solution, immersion into solution containing antibiotics, immersion into synthetic growth factor solution, immersion into solution containing synthetic antibiotics, immersion into extracellular matrix solution, immersion into simulated extracellular matrix solution, immersion into growth factor solution with mammal cells, immersion into solution containing antibiotics and mammal cells, immersion into synthetic growth factor solution with mammal cells, immersion into solution containing synthetic antibiotics and cells, immersion into extracellular matrix solution with cells, immersion into simulated extracellular matrix solution with cells.

The implant can be in the form of a wire, a rod, a bent wire, a spring, a thread, a string, a cylinder, a cuboid, a rope, a mesh, a scaffold, a coil, a screw, a spiral, a helix, a double helix, a multiple helix, a plate, the shape of a part or a whole of the target tissue to be generated or regenerated, an irregular shape, a portion of the a single or a multiple of the aforementioned shapes, a modification of a single or a multiple of the aforementioned shapes, a single or a multiple of the aforementioned shapes with single or multiple holes, a single or a multiple of the aforementioned shapes with single or multiple rings, a single or a multiple of the aforementioned shapes with single or multiple hooks, or a combination thereof.

In one embodiment, part of the implant is bent inside the body at the time of implantation.

In a further aspect of the current invention, the implant may be implanted into a part of the body other than the ultimate target site before being retrieved and put at the target site of generation/regeneration. For example, the material may be pre-implanted subcutaneously to generate an initial layer of fibrous tissue, before implantation into the target site such as ligament. The time period between the initial implantation at a non-target site to the time of retrieval and re-implantation at a target site may be, for example, from 3 minutes to 3 years, or preferably 15 minutes to 1 year, 1 hour to 6 months, or 1 day to 2 months.

In a further aspect, the surface modification may act on the whole surface of the implant, or only a portion of the implant surface.

Aspects and/or embodiments of the subject invention may have one or more of the following advantages. The induction of fibrosis allows the recruitment of cells and collagen formation without, or with less artificially added cells, which greatly reduces the time and cost for the generation or regeneration of soft tissue. The surface modification and/or inclusion of non-metallic solid improves the corrosion properties by increasing or decreasing the corrosion resistance, depending on the specific application. The surface modification and/or inclusion of non-metallic solid increases or decreases the rate of gas production due to implant corrosion, and/or increases or decreases the rate of resorption of the gas, depending on the specific application. The implant shape facilitates the implantation process and/or improves the mechanical properties of the implant, and/or improves the corrosion properties of the implant, depending on the specific application.

Currently, replacement of soft tissues are either achieved by synthetic material with or without cells or growth factors, replacement with allografts, or replacement with autografts. As compared with the current standard synthetic materials (i.e. polymers with or without cells or growth factors) and allografts for the regeneration of soft tissues, the materials used according to the current invention provide better mechanical properties, lower cost, lower chance of infection, shorter preparation time, and the supply is virtually unlimited. As compared to autograft, the supply is virtually unlimited, and does not cause donor-site morbidity, or a decrease in range-of-motion and weakness.

The principle of this invention is simple, yet unconventional. It is a unique combination of two disparate principles (resorbable metallic implant, and the use of a foreign body response to regenerate soft tissue).

Advantageously, it has been determined that the corrosion and resorption of small amounts of Mg and Mg alloys in mice did not lead to significant systemic toxicological effects. Also, toxicological effects are not anticipated in humans. See, Advance Materials Research Vols. 47-50 (2008) pp 604-607, which is incorporated herein, in its entirety, by reference.

Following are examples which illustrate procedures for practicing the invention. These examples should not be construed as limiting. All percentages are by weight and all solvent mixture proportions are by volume unless otherwise noted. AM60B and AM50A are standard magnesium alloy compositions as specified by ASTM Standard B94 (2007) as specified by ASTM International.

EXAMPLE 1

Lathed AM60B magnesium alloy wire, diameter 0.5 mm and length 30 mm, polished and immersed into 12M sodium hydroxide solution for 10 minutes, is further immersed into sterile DMEM for 1 hour. The material is then implanted subcutaneously for 30 days, retrieved, and implanted into a ligament defect site to replace or reinforce a broken ligament.

EXAMPLE 2

Extruded AM50A magnesium alloy wire, diameter 0.3 mm and length 100 mm, folded at the mid-point and then folded again at the new mid-point resulting in a new length of 50 mm, polished and immersed into 12M sodium hydroxide solution for 10 minutes, is further immersed into sterile DMEM for 1 hour. The material is then implanted subcutaneously for 30 days, retrieved, and implanted into a ligament defect site to replace or reinforce a broken ligament.

EXAMPLE 3

99.99% pure magnesium mesh, size 80 mm by 80 mm, immersed into 12M sodium hydroxide solution for 1 minute, is further immersed into sterile phosphate-buffered saline for 1 hour. The material is then implanted into the body to seal the body wall defect which causes organ protrusion at the abdomen.

EXAMPLE 4

AZ31hp magnesium alloy plate, thickness 0.3 mm, width 3 mm, length 20 mm, with rounded corners, with drill holes of 0.7 mm diameter and centred at 2 mm and 5 mm from the terminals, is polished and immersed into 12M potassium hydroxide for 5 minutes. The material is then washed under running sterile distilled water for 5 minutes. The material is then implanted subcutaneously for 60 days. The material is then retrieved and implanted again into a small ligament defect site to replace a broken ligament, using four AZ31hp screws for anchorage onto the adjacent bones.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

We claim:

1. A method for generating or regenerating soft tissue, membranous tissue or an organ, in whole or in part, within a patient in need of generating or regenerating soft tissue, membranous tissue or an organ at a target site, wherein said method comprises implanting, into the patient, a bioresorbable implant comprising a bioresorbable metal, semi-metal, or alloy thereof, wherein the implant contains no more than 40% non-metallic solid,
    wherein before implantation in the target site, the implant is initially implanted at a location in the patient other than the target site of generation or regeneration for a period of at least 1 hour, the implant is then retrieved and re-implanted at the target site,
    wherein said implant induces fibrosis within the patient, and wherein the fibrosis contributes to the generation or regeneration of the soft tissue, membranous tissue or organ, in whole or in part.

2. The method, according to claim 1, wherein before implantation at the target site the said implant is initially placed at a location in the patient other than the target site of generation or regeneration for a period of at least 1 day.

3. The method, according to claim 1, wherein the patient is a human.

4. The method according to claim 1, wherein the implant is bent during the implantation process.

5. A method according to claim 1, wherein the non-metallic solid is selected from carbonate compounds, phosphate compounds, non-metallic compounds of a metallic element, non-metallic compounds of a semimetallic element polymers, anticoagulants, and combinations thereof, and wherein the implant is adapted for use in the body of a mammal.

6. The method according to claim 5, wherein the non-metallic solid is in the form of powder, fiber, film, crystal, nanocrystal, nanoparticle, nano-film or nano-fiber.

7. The method according to claim 1, used to generate or regenerate soft tissues for hernia correction.

8. The method according to claim 1, wherein said implant comprises magnesium, a magnesium alloy, tungsten, a tungsten alloy, zinc, a zinc alloy, aluminum, an aluminum alloy, iron, an iron alloy, steel, manganese, a manganese alloy, calcium, a calcium alloy, zirconium, a zirconium alloy, silicon or a silicon alloy.

9. The method according to claim 1 wherein said implant is surface modified with a metallic material, a semi-metallic material, a non-metallic material, a metallic element in non-metallic or semi-metallic form, a non-metallic element in metallic or semi-metallic form, a semi-metallic element in non-metallic or metallic form, no additional material, or a combination thereof.

10. The method according to claim 9, wherein the surface modification comprises one or more of the following: oxidation, nitriding, solution immersion, anodization, deposition, electrolytic deposition, precipitation, immersion into molten metal, immersion into molten alloy, immersion into molten semi-metal, immersion into collagen, immersion into organic material, plasma immersion, plasma deposition, plasma spraying, flame spraying, chemical vapour deposition, physical vapour deposition, powder deposition, powder immersion, plasma immersion, plasma immersion ion implantation, electric arc deposition, painting, coating, heat treatment, cold treatment, thermomechanical processing, polishing, diffusion alloying, melt alloying, incubation in cell culture condition, and sterilization.

11. The method according to claim 10, wherein the solution immersion comprises one or more of the following: alkali treatment, hot alkali treatment, phosphate buffered saline immersion, cell culture medium immersion, body fluid immersion, simulated body fluid immersion, serum immersion, phosphate solution immersion, acid treatment, immersion into collagen solution, immersion into organic material solution, immersion into growth factor solution, immersion into solution containing antibiotics, immersion into synthetic growth factor solution, immersion into solution containing synthetic antibiotics, immersion into extracellular matrix solution, immersion into simulated extracellular matrix solution, immersion into growth factor solution with mammal cells, immersion into solution containing antibiotics and mammal cells, immersion into synthetic growth factor solution with mammal cells, immersion into solution containing synthetic antibiotics and cells, immersion into extracellular matrix solution with cells, and immersion into simulated extracellular matrix solution with cells.

12. The method according to claim 1, wherein the implant is in the form of a wire, a rod, a bent wire, a spring, a thread, a string, a cylinder, a cuboid, a rope, a mesh, a scaffold, a coil, a screw, a spiral, a helix, a double helix, a multiple helix, a plate, the shape of a part or a whole of the target tissue to be generated or regenerated, an irregular shape, a portion of a single or a multiple of the aforementioned shapes, a modification of a single or a multiple of the aforementioned shapes, a single or a multiple of the aforementioned shapes with single or multiple holes, a single or a multiple of the aforementioned shapes with single or multiple rings, a single or a multiple of the aforementioned shapes with single or multiple hooks, or a combination thereof.

13. The method according to claim 1, used to generate or regenerate an internal organ, in whole or in part.

14. The method according to claim 1, wherein the soft tissue or membranous tissue is not cardiovascular tissue or an internal organ.

15. The method according to claim 14, used to generate or regenerate tissue for hernia correction.

16. The method according to claim 1, used to generate or regenerate cardiovascular tissue.

17. The method according to claim 1, used to generate or regenerate skin.

18. The method according to claim 1, used to generate or regenerate a ligament, tendon, or periodontal fiber.

19. The method according to claim 1, wherein the implant is manufactured by die casting, investment casting, solvent casting, injection moulding, compression moulding, blow moulding, extrusion, intrusion, laminating, sintering, forging, stamping, welding, lathing, tooling, machining, or a combination thereof.

20. The method, according to claim 1, wherein the implant comprises a non-metallic solid.

21. The method according to claim 20, wherein the non-metallic solid is carbon, carbonate compound, phosphate compound, non-metallic compound of metallic element, non-metallic compound of semi-metallic element, polymer, anticoagulant, or a combination thereof.

* * * * *

UNITED STATES PATENT AND TRADEMARK OFFICE
CERTIFICATE OF CORRECTION

PATENT NO.        : 8,172,908 B2                                        Page 1 of 1
APPLICATION NO.   : 12/342812
DATED             : May 8, 2012
INVENTOR(S)       : Wing Yuk Ip et al.

It is certified that error appears in the above-identified patent and that said Letters Patent is hereby corrected as shown below:

Column 9,
Line 42, "element polymers" should read --element, polymers--

Signed and Sealed this
Tenth Day of July, 2012

David J. Kappos
*Director of the United States Patent and Trademark Office*